(12) United States Patent
Murdock et al.

(10) Patent No.: US 6,290,986 B1
(45) Date of Patent: Sep. 18, 2001

(54) METHOD AND COMPOSITION FOR TRANSDERMAL ADMINISTRATION OF PHARMACOLOGIC AGENTS

(75) Inventors: Robert W. Murdock, Selah; C. Donald Williams, Yakima, both of WA (US)

(73) Assignee: Pharmaceutical Applications Associates, LLC, Yakima, WA (US)

(*) Notice: Subject to any disclaimer, the term of this patent is extended or adjusted under 35 U.S.C. 154(b) by 0 days.

(21) Appl. No.: 09/106,684

(22) Filed: Jun. 29, 1998

Related U.S. Application Data

(63) Continuation-in-part of application No. PCT/US97/19651, filed on Oct. 24, 1997, and a continuation-in-part of application No. 08/957,485, filed on Oct. 24, 1997, now abandoned.
(60) Provisional application No. 60/029,120, filed on Oct. 24, 1996.

(51) Int. Cl.⁷ ............................................. A61F 13/00
(52) U.S. Cl. .................... 424/449; 424/447; 424/448; 424/484; 514/78
(58) Field of Search ............................ 424/484, 447, 424/448, 449; 514/78

(56) References Cited

U.S. PATENT DOCUMENTS

| | | | |
|---|---|---|---|
| 4,395,420 | 7/1983 | Bernstein | 424/278 |
| 4,668,232 | 5/1987 | Cordes et al. | 604/897 |
| 4,788,063 | 11/1988 | Fisher et al. | 424/449 |
| 4,794,000 | 12/1988 | Ecanow | 424/457 |
| 4,876,260 | 10/1989 | Fisher et al. | 514/278 |
| 4,908,389 | * 3/1990 | Mahjour et al. | 514/772 |
| 4,914,084 | 4/1990 | Ecanow | 514/6 |
| 4,963,367 | 10/1990 | Ecanow | 424/485 |
| 4,981,858 | 1/1991 | Fisher et al. | 514/278 |
| 5,106,831 | 4/1992 | Fisher et al. | 514/2 |
| 5,292,499 | 3/1994 | Evans et al. | 424/45 |
| 5,326,570 | 7/1994 | Rudnic et al. | 424/458 |
| 5,356,934 | 10/1994 | Robertson et al. | 514/649 |
| 5,446,070 | 8/1995 | Mantelle | 514/772.6 |
| 5,478,828 | 12/1995 | Mattson et al. | 514/253 |
| 5,560,910 | 10/1996 | Crandall | 424/94.63 |
| 5,601,839 | 2/1997 | Quan et al. | 424/448 |
| 5,639,740 | 6/1997 | Crandall | 514/78 |
| 5,654,337 | 8/1997 | Roentsch et al. | 514/570 |
| 5,656,286 | 8/1997 | Miranda et al. | 424/449 |
| 5,693,337 | 12/1997 | Suzuki et al. | 424/450 |
| 5,708,035 | 1/1998 | Young et al. | 514/649 |
| 5,837,289 | * 11/1998 | Grasela et al. | 424/484 |
| 5,885,597 | 3/1999 | Botknecht et al. | 424/401 |

FOREIGN PATENT DOCUMENTS

| | | | |
|---|---|---|---|
| WO 89/00077 | 1/1989 | (WO) | B01F/17/00 |
| WO 93/01812 | 2/1993 | (WO) | A61K/31/415 |
| WO 95/28152 | 10/1995 | (WO) | A61K/31/135 |

* cited by examiner

*Primary Examiner*—Thurman K. Page
*Assistant Examiner*—Lakshmi Channavajjala
(74) *Attorney, Agent, or Firm*—Lahive & Cockfield, LLP; Gjulio A. DeConti, Jr.; Maria C. Laccotripe

(57) ABSTRACT

A method and composition for transdermal delivery of pharmaceuticals or combinations of pharmaceuticals is provided. The pharmaceuticals are delivered using a matrix of a lecithin gel such as a lecithin organogel. A number of psychopharmaceuticals can be used including fluoxetine, sertraline, carbamazepine, paroxetine, amitriptyline, trazadone, venlafaxine, propranolol, buprobrion, valproic acid, nefazodone, ketoprofen, gabapentin, piroxican, doxepin, guaifenesin, pemoline and doxepin and combinations.

11 Claims, 1 Drawing Sheet cpt 90862 Medication Management (cdw ver. 4-24-95)                                    90862.DOC Patient: _____ Date _____

Current Medication:   1) _____
                      2) _____
                      3) _____
                      4) _____
                      5) _____
                      6) _____

Diagnoses:   Axis 1: _____
                                                     Axis 3: _____
             Axis 2: _____          GAF _____

Subjective: _____
_____
_____
_____
_____
_____

Objective :   APPEARANCE _____        AFFECT _____
              SPEECH _____        CONCENTRATION _____
              MEMORY _____        IRRITABILITY _____
              APPETITE _____        A/V HALLUC. _____
              CRYING SPELLS _____        ENERGY LEVEL _____
              SLEEP _____        WEIGHT _____
SIDE EFFECTS: _____

RESPONSE OF DEPRESSION SYMPTOMS TO MEDICATIONS:
        EXCELLENT          GOOD           FAIR          POOR          N/A

RESPONSE OF ANXIETY SYMPTOMS TO MEDICATIONS:
        EXCELLENT          GOOD           FAIR          POOR          N/A

CONCURRENT MEDICATION CONDITIONS: _____
_____

ASSESSMENT: _____
_____
_____
_____

PLAN:  1) Continue meds: _____
       2) Change dosage: _____
       3) New Med: _____
       4) _____

LAB STUDIES ORDERED: _____
OTHER: _____

METHOD AND COMPOSITION FOR TRANSDERMAL ADMINISTRATION OF PHARMACOLOGIC AGENTS

The present application is a continuation-in-part of PCT/US97/19651 and of U.S. patent application Ser. No. 08/957,485, filed Oct. 24, 1997, now abandoned, which claims priority based on provisional application Ser. No. 60/029,120 filed Oct. 24, 1996.

The present invention is directed to transdermal administration of pharmacologic agents, and in particular to transdermal administration of drugs including antidepressant serotonin specific reuptake inhibitors (as SSRIs) such as fluoxetine, antidepressants such as buprorion and reboxetine, tricyclic antidepressant medications that have neuropathic pain treatment efficacy such as amitriptyline and doxepin, mood stabilizers such as carbamazepine, or valproic acid, Attention Deficit Hyperactivity Disorder (ADHD) medications such as pemoline anti-inflammatory or analgesic medications such as ketoprofen or piroxicam, treatments for impotence such as sildenafil and or anti-convulsants believed to possess neuropathic pain treatment efficacy such as gabapentin, carbamazepine, or combinations thereof such as using a gel matrix, preferably a lecithin organogel and/or a polymer gel.

BACKGROUND INFORMATION

In the past, patients suffering from a wide variety of conditions have been successfully treated by administration of pharmacologic agents. A vast majority of such patients receive doses of these agents orally. Unfortunately, in some situations, oral administration of such agents has been infeasible or ineffective. In some cases, oral administration is associated with side effects, particularly gastrointestinal side effects, sedation, or weight gain which cannot be tolerated well by the patient. In other cases, malabsorption of oral preparation have resulted in subtherapeutic plasma levels. In other cases, the agents have relatively short plasma half-lives, necessitating inconveniently frequent dosing. In general, oral delivery involves a time delay as the pharmaceutical is absorbed via the digestive system before entering the bloodstream. A number of agents which have traditionally been administered orally or by injection have been inappropriate or suboptimal for some patients when so-administered.

There are a number of medications which in at least some patients are not tolerated well when orally administered (e.g. which cause undesirable gastrointestinal or other side effects) and/or which provide undesirably high or low concentrations or delayed concentrations in a target tissue. In some cases, dosages which are appropriate for oral administration, upon being distributed more or less uniformly throughout the body, are undesirably low in a particular tissue to achieve desired results. Oral or injection administration may result in to slow or too rapid increase in blood plasma levels, e.g. may involve an undesirably long time delay as the pharmaceutical is absorbed by the digestive system before entering the bloodstream, or may result in a "spike" in blood plasmal levels followed by an undesirably low level, where a more constant level would be preferable. Some pharmaceuticals are particularly prone to cause or contribute to liver damage when administered orally.

One alternative route of administration for selected pharmaceuticals, has been transdermal delivery. Transdermal delivery has been utilized, e.g., for the treatment of high blood pressure, for ischemic heart disease and for hormone replacement. Transdermal delivery is not necessarily appropriate for all types of pharmaceuticals and, it is believed, has not, in general, previously been successfully used, with full effectiveness, for psychopharmacologic or psychotropic agents. Transdermal delivery is accompanied by its own side effects, including a potential for skin irritation, arising from the gel or other matrix, from the pharmaceutical itself, or from the interaction of the pharmaceutical with the matrix. Furthermore, a transdermal system must be configured such that the combination of the matrix and the pharmaceutical does not react with or modify the pharmaceutical, or otherwise render it ineffective, such that the combination provides sufficient diffusion coefficients, such that the delivery system is not adversely affected by expected temperature variations during normal manufacture, transportation, storage and use, such that the gel or other matrix retain the desired viscosity, and such that the pharmaceutical can be properly dispersed or dissolved in the matrix such that components remain homogenous and do not separate (particularly when more than one pharmaceutical is included) and the like.

Although other forms of delivery of pharmaceuticals agents are known, each has its drawbacks. Parenteral (i.e., intravenously or intramuscularly injected) administration is inconvenient and expensive, and is rarely used outside the hospital. Inhalation is believed to be not feasible with psychopharmacologic agents currently in use or with many other pharmaceuticals.

Accordingly, it would be useful to provide a transdermal delivery system effective to provide good transdermal absorption and acceptable plasma blood levels preferably a system which can be adapted for use with a wide variety of different agents for transdermal delivery of effective amounts of such agents at a desired or controlled rate, while preferably avoiding or reducing undesired effects such as liver damage, gastrointestinal side effects, sedation, and weight gain.

SUMMARY OF THE INVENTION

The present invention provides for transdermal delivery of pharmacologic agents, particularly psychopharmacologic, anti-convulsant, anti-inflammatory, analgesic or other agents, by dissolving or dispersing such agents in a gel, preferably a lecithin organogel. In one embodiment, an agent is delivered using a lecithin gel such as a gel formed using lecithin and an organic solvent such as isopropyl palmitate or isopropyl myristate, alcohol, or ethoxy diglycol. In one embodiment, the gel includes or is formed from a polymer such as that sold under the trade name "Pluronic" available from BASF-Wyandotte Corporation, Parsippany, N.J.

BRIEF DESCRIPTION OF THE DRAWING

FIG. 1 is a depiction of an evaluation form used in evaluating an embodiment of the present invention.

DETAILED DESCRIPTION OF THE PREFERRED EMBODIMENTS

One class of psychopharmacologic agents, some of whose members can be administered according to embodiments of the present invention, are serotonin specific reuptake inhibitors (SSRIs). SSRIs are commonly prescribed for patients with diagnoses of mood disorders, some forms of anxiety disorder (particularly panic disorder), obsessive compulsive disorders, some forms of menopausal disorders, and eating disorders (especially bulimia nervosa). Examples of such SSRIs include sertraline (sold under the trade name Zoloft), paroxetine (sold under the trade name Paxil), fluoxetine (sold under the trade name Prozac), venlafaxine (sold under the trade name Effexor), and fluvoxamine (sold under the trade name Luvox). Although many patients tolerate oral administration of these SSRIs, a certain population of patients experience gastrointestinal side effects. Without wishing to be bound by any theory, it is believed that such side effects may be relatively frequent for SSRIs in part because the gastrointestinal system is richly endowed with serotonin receptors and that SSRIs may result in such side effects as alterations in gastric motility, nausea, and diarrhea. Medically healthy individuals may tolerate oral dosing with SSRIs with difficulty, or not at all. Medically compromised patients, for example patients with gastric or duodenal ulcer, ulcerative colitis, irritable colon syndrome or regional enteritis may not be able to tolerate the oral form of these medications and thus, in the absence of alternative administration routes, may be deprived of helpful antidepressant pharmacotherapeutic treatment.

Another class of psychopharmacologic agents which may be administered accordingly to embodiments of the present invention include antidepressants such as buproprion (sold under the trade name Wellbutrin), reboxetine (sold under the trade name Edronax), nefazodone (sold under the trade name Serzone) and trazadone (sold under the trade name Desyrel). Although these antidepressant medications are often well tolerated by the gastrointestinal (GI) system, in some cases, oral preparations have resulted in malabsorption problems or idiosyncratic side effects, which, in some cases, may be avoided by transdermal administration according to embodiments of the present invention, as described more thoroughly below.

Yet another category of psychopharmacologic agents are mood stabilizing medications, examples of which include carbamazepine (sold under the trade name Tegretol) and valproic acid (sold under the trade name Depakote). These agents are used frequently in psychiatric practice as either augmentation medications (to render antidepressants more effective) or as anti-manic medications in the treatment of bipolar mood disorder. They are also used in neurologic practice for the treatment of seizure disorders and for the treatment of certain pain disorders. Many patients have difficulty tolerating the gastrointestinal side effects of these medications, most typically nausea. Such side effects are particularly troublesome for these agents since compliance with rigorously regular medication schedules is of great clinical importance to many of these patients. Accordingly, transdermal delivery according to embodiments of the present invention is particularly helpful in achieving compliance with a regular medication schedule.

Another type of psychopharmaceutical agent are those used for treating Attention Deficit Hyperactivity Disorder (ADHD), one example of which is permoline, sold under the trade name Cylert. Permoline is a medication that is used in the treatment of Attention Deficit Hyperactivity Disorder in children and adults. It is practically insoluble in water, but soluble in ethylene glycol and lipids, making it a good candidate for transdermal administration. Its principal problem in medical practice is its association with chemical hepatitis (hepatotoxicity). Since approximately 80% of orally ingested pemoline goes through the liver prior to reaching the bloodstream (called first pass metabolism), transdermal administration, which bypasses the liver, may offer a significant advantage in reducing liver metabolism. It is anticipated that the incidence of chemical hepatitis might be significantly lower for transdermally administered permoline.

Another type of psychopharmaceutical agent includes dopamine agents, used for treating Parkinson's disease, examples of which are pergolide, sold under the trade name Permax and bromocriptine mesylate, sold under the trade name Parlodel. Oral administration of dopamine agents such as pergolide or bromocriptine mesylate may be sub-optimal because of GI irritation. Accordingly, transdermal delivery of dopamine agents such as pergolide and bromocriptine mesylate, according to embodiments of the present invention, is particularly useful.

Another type of psychopharmaceutical agent are those used for treating depression and/or neuropathic pain, two examples of which are generically available amitriptyline, sold under the trade name Elavil and doxepin sold under the tradename Sinequan. Oral administration of amitriptyline and doxepin may be sub-optimal when high local tissue concentrations are desired. Accordingly, transdermal delivery of amitriptyline and doxepin, according to embodiments of the present invention, is particularly useful.

In some situations, a transdermal composition containing a combination of doxepin or amitriptyline with carbamazepine or gabapentin is useful for treating neuropathic pain. It is believed that transdermal administration of such combination can be advantageous, for at least some patients, as compared to oral administration, because higher local drug concentrations at the sites(s) e.g. of injury can be achieved yielding an improved therapeutic response without systemic side effects such as weight gain, drowsiness, gastrointestinal upset and anticholinergic side effects (which include but are not limited to urinary retention, blurred vision and dry mouth).

Another type of psychopharmaceutical agent are those used for treating hypertension and akathisia, one example of which is propranalol, sold under the trade name Inderal. Oral administration of propranalol may be sub-optimal because of rare GI intolerance or malabsorption. Accordingly, transdermal delivery of propranalol according to embodiments of the present invention is particularly useful.

Another class of pharmaceutical that may be particularly useful for localizing the dosage via transdermal applications are anticonvulsant agents such as generically available carbamazepine and patent protected gabapentin (sold respectively under the trade names Tegretol and Neurontin). Gabapentin is an anticonvulsant agent that is believed to relieve pain by blocking GABA-B neuroreceptor pain sites. Both gabapentin and carbamazepine often relieve muscle spasms, and therefore alleviate chronic pain through that mechanism as well. In oral form, gabapentin has been described as useful for chronic pain and reflex sympathetic dystrophy. It has been found to be useful for alleviating the neuropathic component of pain resulting form cervical, thoracic, and lumbar spinal disk injury. Transdermal application of gabapentin and carbamazepine are particularly effective means of obtaining higher local tissue concentrations of the medications, avoiding many systemic side effects, which can include fatigue, lethargy, and dizziness. The combinations described in some of the examples below are means of adding to the antispasmodic and analgesic properties of the gabapentin and carbamazepine.

Another type of pharmaceutical that may be useful for transdermal application are those used for their analgesic and anti-inflammatory properties, or pain relief, such as ketoprofen and other non-steroidal anti-inflammatory drugs. For some patients, combinations of ketoprofen, doxepin, guaifenesin and/or carbamazepine have been demonstrated to be useful, e.g., for the treatment of superficial inflammation and swelling in combination with neuropathic pain, for example, in carpal tunnel syndrome, cervical disk and lumbar disk degenerative disease, occipital neuralgia, knee injuries including cartilage tears and joint surface damage, and similar degenerative processes involving the ankle and elbow. It has been demonstrated that administration of a combination of ketoprofen with other agents, particularly doxepin, gabapentin, and guaifenesin, can, for a majority of patients be useful as compared to oral agents, because it is believed that a composition combining ketoprofen with these agents provides substantially synergistic results, i.e. such that results are greater than the sum of results form ketoprofen alone in a transdermal application plus results from such additional components. It appears that the synergistic effect is most apparent when actual superficial swelling and inflammation is present; otherwise, use of the doxepin in combination with an anticonvulsant such as carbamazepine or gabapentin produces results that are not enhanced by the addition of ketoprofen. In some cases, guaifenesin has yielded a significant improvement in reduction of spasms, superior to that achieved with either carbamazepine or gabapentin. Guaifenesin is a centrally acting muscle relaxant. It is soluble in water, 1 gm at 25 degrees, and soluble in some organic solvents. Thus it appears to be on the border of oil and water solubility. Without wishing to be be bound by any theory, it is believed this attribute may help explain, at least in part, the utility of guaifenesin (and, for similar reasons, fluoxetine) as a transdermal agent.

Another type of pharmaceutical that may be useful for transdermal administration includes pharmaceuticals used in treatment of impotence such as sildenafil, sold under the tradename Viagra. It is believed that transdermal administration of sildenafil may be useful, for at least some patients, as compared to oral administration which has been found, in at least some situations, to be associated with gastrointestinal side effects. Reports of deaths of sildenafil users may be an additional reason to consider a transdermal application method.

According to embodiments of the present invention, tablets, capsules or other preparations of psychopharmacologic agents or other pharmaceuticals, e.g., intended for oral delivery, were crushed and dispersed or dissolved in a gel formed of soya lecithin and isopropyl palmitate or isopropyl myristate, alcohol, or ethoxy diglycol. In some cases, Pluronic gel, formed of Pluronic such as Pluronic F127, potassium sorbate and water was formed.

Without wishing to be bound by any theory, it is believed the degree to which pharmaceutical compounds will successfully diffuse or be transdermally transported through the skin into blood vessels is related in part to properties of lipid solubility. Lipid solubilities of pharmaceuticals are, to some extent, inversely proportional to their aqueous solubility, which is in part a function of the compound's polarity. Therefore, fluoxetine hydrochloride, which has limited aqueous solubility and apparent moderate lipid solubility, is transdermally transported whereas venlafaxine and buproprion, it is currently believed, are not transported particularly effectively. The oil-water coefficient is believed to be partially predictive of the degree to which a given compound, theoretically, can be transdermally transported. However, because the physical properties of these complex organic compounds are neither fully determined nor documented and because other factors may be significant, (any some of which are understood) it is not possible to predict, other than in approximate (general terms, their potential for (and thus the advisability of testing for) transdermal transport. These physical properties are particularly complex and difficult to forecast, e.g., because of the molecular mechanical release and retention properties of organogel lecithin, which contains a very long chain polymer (Pluronic) that has been demonstrated to vary widely, e.g., with temperature, percentage composition of the gel, and concentration of the pharmaceutical.

Detailed examples of the preparation are provided below, along with examples of results obtained or expected from transdermal administration to human patients. Typically, the gel preparation was or will be applied to either volar surface of the lower arm of the patient, the post-auricular (behind the ear) region, or at the painful site when treating neuropathic pain. Laboratory measures of plasma blood levels were or will be obtained as shown in the examples below. The results generally demonstrate or are expected to demonstrate good absorption transdermally using lecithin organogel matrix as the vehicle. In circumstances where the objective was to treat neuropathic or chronic pain, only local effects were required and plasma blood levels were not obtained. Some patients were or will be evaluated by means of a structured evaluation form (FIG. 1), completed at a frequency of at least one time per week. Patients were or will be evaluated both for all the present symptoms as well as any side effects from currently administered medications. This is believed to make it possible to note changes on an ongoing basis. In general, for psychiatric patients, those with the most clear cut and uncomplicated diagnoses of major depression experienced, or are expected to experience, the best results. Patients with severe personality disorders or with concealed substance abuse disorders generally did less well.

EXPERIMENTAL

EXAMPLE 1

One hundred grams of lecithin soya (granular) and 0.66 grams sorbic acid (NF-FCC powder) were dispersed in 100 grams (117 milliliters (mL)) of isopropyl palmitate NF and allowed to stand overnight. Approximately 220 milliliters of lecithin-isopropyl palmitate in a form of a liquid of a syrup consistency was formed.

EXAMPLE 2

One hundred grams of lecithin soya (granular) and 0.66 grams sorbic acid (NF-FCC powder) is dispersed in 100 grams (117 milliliters) of isopropyl myristate NF and allowed to stand overnight. Approximately 220 milliliters of lecithin-isopropyl myristate in a form of a liquid of a syrup consistency is formed.

EXAMPLE 3

A beaker was prepared by measuring to a volume of 100 milliliters. It was considered important to measure the volume accurately rather than using beaker markings. An amount of Pluronic F127 NF (20 grams for a 20 percent gel, 30 grams for a 30 percent gel, 40 grams for a 40 percent gel) was mixed with 0.3 grams potassium sorbate NF. Refrigerated purified water was added in an amount sufficient to bring the volume to 100 milliliters. When all of the granules had been wet the gel was refrigerated. Solution took place upon cooling, taking 12 to 24 hours. The resulting 100 milliliters of Pluronic gel was kept refrigerated, since the gel will solidify at room temperature.

EXAMPLE 4

Nine grams of carbamazepine in tablet form was ground in mortar and pestle. 4.3 milliliters of ethoxy diglycol was added and mixed to form a creamy paste. 13.2 milliliters of soya lecithin was added and mixed until smooth. The resulting 24 cc of solution was put into a 60 cc syringe. About 36 cc Pluronic F127 gel 20 percent (made according to Example 3) was placed in another syringe. The material was mixed well between syringes to yield 60 cc of carbamazepine organogel having a strength of 150 milligrams (mg) per milliliter. In some cases, the mixture was run through an ointment mill to reduce particle size.

EXAMPLE 5

Sixty 100 milligram tablets of buprorion were ground and strained to form a fine powder. The buprorion powder was dissolved in 30 cc purified water, placed in a filter and washed with 10 to 20 cc purified water. The filtrate was used to make a 20 percent Pluronic gel using the procedures from Example 3, substituting filtrate for an equivalent volume of water, and stored in a refrigerator. Thirteen milliliters of soya lecithin was mixed with one-half the buprorion Pluronic gel and mixed between syringes to form a first batch. Thirteen milliliters of soya lecithin was mixed with the second half of the buprorion Pluronic gel and mixed between syringes to form a second batch. To each batch was added sufficient Pluronic gel F127 (made according to example 3) to yield a total of two 60 cc batches of buprorion HCl organogel having a strength of 15 milligrams per milliliter.

EXAMPLE 6

600 milligrams of fluoxetine HCl (in the form of thirty 20 milligram capsules) was placed in a beaker and dissolved in approximately 18 cc of 95 percent ethyl alcohol. The solution was filtered through a filter funnel using fine filter paper. The residue was washed with 95 percent alcohol. The filtrate was heated, maintaining a temperature less than 85° C., to evaporate the alcohol to concentrate to 1 to 2 milliliters. 600 milligrams of isopropyl palmitate was combined with 600 milligrams of soya lecithin (granular), set aside and allowed to liquefy. Upon liquefaction, a thick syrupy consistency was obtained. 1.2 grams of the mixture was drawn into a 10 milliliter syringe and the alcoholic solution of fluoxetine HCl was drawn into another syringe. The two syringes were attached together with a Luer-Luer adapter and the gel was thoroughly mixed. All of the organogel was then transferred into one syringe and the empty syringe was disconnected. Sufficient quantity of 20 percent Pluronic F127 gel (formed as described in Example 3) was drawn into the empty syringe to make a total of 6 milliliters when added to the volume in the other syringe. A Luer-Luer adapter was attached and the contents of the two syringes was remixed until a smooth creamy mixture was obtained. All the mixture was transferred into one syringe, the empty syringe was removed and the Luer-Luer adapter was removed.

A Luer-oral adapter was attached to the mixture and transferred to six 1 milliliter oral syringes, was filled with 1 milliliter of the gel. In this way, each syringe contained five 20 milligram doses, or ten 10 milligram doses to yield a total of 60 doses of fluoxetine in lecithin organogel having a strength of 10 milligrams per 0.1 milliliters.

EXAMPLE 7

Twelve 250 milligram tablets of nefazadone were crushed in a mortar and pestle and put through a strainer. 4.8 milliliters of ethoxy diglycol (8 percent) was added and mixed. In cases in which all particles were not dissolved, 2 milliliters of Pluronic were added and mixed. 13.6 milliliters of soya lecithin were added and mixed. The resulting mixture was put into syringes with a Luer adapter and mixed well. Sufficient Pluronic F127 gel, prepared according to Example 3, was added to achieve a volume of 60 cc and mixed well to yield 60 cc of nefazadone organogel having a strength of 50 milligrams per milliliter.

EXAMPLE 8

Thirty 40 milligram tablets of paroxetine were crushed and run through a strainer, discarding green coating material. 4.8 milliliters of ethoxy diglycol was added to the powder and mixed in a mortar and pestle. Forty milliliters of Pluronic F127 gel 20 percent, formed according to Example 3, was added in graduated amounts to the powder and mixed until smooth using a spatula. 13.2 milliliters of soya lecithin was added and mixed well and the resulting material placed into syringes and sufficient quantity of Pluronic gel was added to bring the volume to 60 milliliters. In those such cases where particle size of the resulting material was too large, the cream was run through an ointment mill to yield 60 milliliters of paroxetine organogel having a strength of 20 milligrams per milliliter.

EXAMPLE 9

Thirty 100 milligram tablets of sertraline were crushed into a fine powder and strained, discarding the yellow coating. Sufficient amount of Pluronic F127 gel 20 percent (formed according to Example 3) was added to achieve a volume of 38 milliliters and mixed well in a mortar and pestle until a smooth cream was achieved. This material was placed into syringes and mixed between the syringes to obtain a compact cream. 13.2 milliliters of soya lecithin was added and mixed well between the syringes using about 20 pumps. Sufficient quantity of Pluronic F127 gel 20 percent was added to yield 60 milliliters of sertraline gel having a strength of 15 milligrams per milliliter.

EXAMPLE 10

Venlafaxine hydrochloride has a solubility in water of 572 mg/mL (adjusted to ionic strength of 0.2 M with sodium chloride). Forty-five 100 milligram tablets of venlafaxine were crushed and put through a strainer. The powder was dissolved in 15 cc purified water, the solution placed into a filter and washed with 10 cc purified water. The filtrate was used to make a 20 percent Pluronic gel using the procedures of Example 3 (substituting the filtrate for an equivalent amount of water) and placed into a refrigerator overnight. 13.2 milliliters of soya lecithin were drawn into a syringe with a Luer loc. The venlafaxine Pluronic gel was drawn into another syringe coupled to the first syringe and mixed well. Sufficient Pluronic F127 gel was added to achieve a volume of 60 cc with a strength of 75 mg. per cc.

EXAMPLE 11

15 grams of sodium valproate (Depakote) was ground in mortar and pestle. 4 mL of ethoxy diglycol was added and mixed well to form a creamy paste. 19.8 mL of soya lecithin was added and mixed until smooth. The resulting 24 cc of solution was put into 2 syringes with a Luer Loc and mixed well. The mixture was divided so that half is in each syringe. Using another 60 cc syringe, Pluronic 30% gel was added to each to bring each syringe to a volume of 45 mL.

EXAMPLE 12

Paroxetine hydrochloride has a solubility in water of 5.4 mg/mL. Paroxetine (Paxil) gel was prepared, according to the procedures of example 8. A dosage of 40 mg per day was self-administered by a 59 year old male patient by application to the skin, for a period of at least 1 hour. No skin irritation was reported. After 210 days, blood was drawn and blood serum level of Paxil was determined to be 0 nanograms (ng) per mL, while typical reference levels are 49±26 ng/mL, indicating possible poor absorption or lab error. Clinical evaluation of the patient over a 210 day period of such transdermal administration indicated benefit to patient without GI side effects similar to that noted with oral preparation.

EXAMPLE 13

Sertraline hydrochloride is slightly soluble in water and isopropyl alcohol and sparingly soluble in ethanol. Sertraline (Zoloft) gel was prepared, according to the procedures of example 9. A dosage of 100 mg per day was self-administered by a 54 year old female patient by application to the skin, for a period of at least 1 hour. No skin irritation was reported. After 19 days, blood was drawn and blood serum level of Zoloft was determined to be 5 ng/mL, while typical reference levels are 30–200 mg/mL indicating possible limited absorption or lab error.

EXAMPLE 14

Fluoxetine hydrochloride has a solubility in water of 14 mg/mL. Fluoxetine (Prozac) gel was prepared, according to the procedures of example 6. A dosage of 20 mg per day was self-administered by a 54 year old female patient by application to the skin, for a period of at least 1 hour. No skin irritation was reported. After 7 days, blood was drawn and blood serum level of fluoxetine was determined to be 45 ng/ml, while the plasma level of the primary active metabolite norfluoxetin was also 45 ng/ml. There was evidence of patient benefit from the clinical evaluation.

EXAMPLE 15

Carbamazepine is practically insoluble in water and soluble in alcohol and in acetone. Carbamazepine (Tegretol) gel was prepared, according to the procedures of example 4. A dosage of 400 mg per day was self-administered by a 55 year old male patient by application to the skin, for a period of at least 1 hour. No skin irritation was reported. After 120 days, blood was drawn and blood serum level of Tegretol was determined to be 4.6 micrograms ($\mu g$) per mL, while typical therapeutic levels arc 4–10 $\mu g$/mL indicating good absorption. There were no GI side effects and the patient demonstrated clinical improvement.

EXAMPLE 16

Carbamazepine (Tegretol) gel was prepared, according to the procedures of example 4. A dosage of 200 mg per day was self-administered by a 53 year old male patient by application to the skin, for a period of at least 1 hour. No skin irritation was reported. After 60 days, blood was drawn and blood serum level of Tegretol was determined to be 10.8 $\mu g$/mL, while typical therapeutic levels are 4–10 $\mu g$/mL indicating excellent absorption. There were no GI side effects and the patient demonstrated clinical improvement.

EXAMPLE 17

Sertraline (Zoloft) gel was prepared, according to the procedures of example 9. A dosage of 50 mg per day was self-administered by a 53 year old male patient by application to the skin, for a period of at least 1 hour. No skin irritation was reported. After 63 days, blood was drawn and blood serum level of Zoloft was determined to be 23 ng/mL, while typical reference levels are 30–200 mg/mL. The patient demonstrated a good clinical response without GI side effects.

EXAMPLE 18

Carbamazepine (Tegretol) gel was prepared, according to the procedures of example 4. A dosage of 200 mg per day was self-administered by a 47 year old male patient by application to the skin, for a period of at least 1 hour. No skin irritation was reported. After 91 days, blood was drawn and blood serum level of Tegretol was determined to be less than 0.5 $\mu g$/mL, while typical therapeutic levels are 4–10 $\mu g$/mL, indicating poor absorption, lab error, or patient non-compliance.

EXAMPLE 19

Buproprion is highly soluble in water. Buproprion (Wellbutrin) gel was prepared, according to the procedures of example 5. A dosage of 100 mg per day was self-administered by a 47 year old male patient by application to the skin, for a period of at least 1 hour. No skin irritation was reported. After 44 days, blood was drawn and blood serum level of Wellbutrin was determined to be less than 0.5 ng/mL, while typical therapeutic levels are 10–30 indicating poor absorption, lab error, or patient non-compliance.

EXAMPLE 20

Fluoxetine gel was prepared, according to the procedures of example 6. Typically, a total daily adult dosage of fluoxetine as applied to the skin according to the present invention is between about 20 mg and 200 mg, more preferably between about 120 mg and about 200 mg. Dosages for non-adults and/or non-human mammals may need to be adjusted, e.g. proportionally to body weight. A dosage of 20–60 mg per day was self-administered by 5 patients, including that of example 13 and also including a 44 year old male patient, a 53 year old female patient, a 47 year old male patient and a 36 year old female patient by application to the skin, for a period of at least 1 hour. No skin irritation or gastrointestinal side effects were reported. Clinical evaluation of the patients over a 30–180 day period of such transdermal administration indicated a clinical response ranging from complete remission of symptoms to moderate improvement.

EXAMPLE 21

Fluoxetine gel was prepared, according to the procedures of example 6. A dosage of 80–160 mg per day was self administered by a 50 year old female by application to the skin, for a period of at least 1 hour. No skin irritation was reported. After 7 days at the 80 mg dosage level blood was drawn and the blood serum of fluoxetine was determined to be 34 ng/mL fluoxetine and 25 ng,/mL norfluoxetine, while typical reference levels are 50–480 ng/mL, indicating good absorption. There was evidence of patient benefit from the clinical evaluation. The dosage was then increased to 160 mg per day and administered by the same method. After 7 days at the 160 mg dosage level blood was drawn and the blood serum level of fluoxetine was determined to be 90 ng/mL fluoxetine and 25 ng/mL norfluoxetine, indicating good absorption. There was evidence of increased patient benefit at this higher dosage level which correlated positively with the higher plasma level. The patient has been receiving the medication continuously for a period of 5 months.

EXAMPLE 22

Fluoxetine gel was prepared, according to the procedures of example 6. A dosage of 80–160 mg/day was self administered by a 38 year old female by application to the skin, for a period of at least 1 hour. No skin irritation was reported. After 7 days at the 80 mg dosage level, blood was drawn and the blood serum level of fluoxetine was determined to be 25 ng/mL of fluoxetine and 25 ng/mL norfluoxetine. There was evidence of patient benefit from the clinical evaluation. The dosage was then increased to 160 mg per day and administered by the same method.

EXAMPLE 23

Sertraline (Zoloft) gel was prepared, according to the procedures of example 9. A dosage of 50–200 mg per day was self-administered by 6 patients, including those of examples 12 and 16 and also including a 60 year old male patient, a 53 year old male patient, a 48 year old male patient, a 38 year old male patient and a 47 year old male patient, by application to the skin, for a period of at least 1 hour. No skin irritation or gastrointestinal side effects were reported. Clinical evaluation of the patients over a 7–90 day period of such transdermal administration indicated responses ranging from complete resolution of depression to no noticeable response.

EXAMPLE 24

Carbamazepine (Tegretol) gel was prepared, according to the procedures of example 4. A dosage of 200–400 mg per day was self-administered by 6 patients, including those of examples 14, 15 and 17, and also including a 48 year old female patient, a 48 year old male patient and a 54 year old female patient, by application to the skin, for a period of at least 1 hour. No skin irritation or gastrointestinal side effects were reported. The clinical evaluation of the patients over a 30–300 day period of such transdermal administration indicated responses ranging from moderate improvement to no positive clinical response.

EXAMPLE 25

Paroxetine (Paxil) gel was prepared, according to the procedures of example 8. A dosage of 20 mg per day was self-administered by the patient of example 12 as well as by a 15 year old female patient by application to the skin, for a period of at least 1 hour. No skin irritation was reported. Clinical evaluation of the patients over a 30–210 day period of such transdermal administration indicated equivocal clinical improvement of the depression which may (or may not) have been related to the transdermally administered Paxil.

EXAMPLE 26

Five 150 mg tablets of amitriptyline were crushed and run through a strainer. The powder was put into syringes with a Luer Loc and mixed well with 2 mL ethoxy diglycol. About 6 mL Pluronic Gel 20% was added and mixed well. 6.6 mL Soya Lecithin was added and mixed well. This mixture was thinned to 30-mL, total volume with Pluronic Gel 20% and mixed well. The resulting mixture having a strength of 25 mg/mL was placed in appropriate dispensing device.

EXAMPLE 27

Amitriptyline (Elavil) gel was prepared, according to the procedure of example 26. A dosage of 25 mg per day was self-administered by a 47 year old male patient. Administration was by application to the skin, for a period of at least 1 hour. No skin irritation or gastrointestinal side effects were reported. Clinical evaluation of the patients over a 100 day period of such transdermal administration indicated an apparently good clinical response, comparable to that achieved with oral medication.

EXAMPLE 28

Trazodone (Desyrel) gel was prepared, according to a procedure similar to that of example 7. A dosage of 50–150 mg per day was self-administered by 2 patients, including a 36 year old female patient and a 47 year old male patient. Administration was by application to the skin, for a period of at least 1 hour. No skin irritation or gastrointestinal side effects were reported. Clinical evaluation of the patients over a 42–90 day period of such transdermal administration indicated a good to excellent clinical response.

EXAMPLE 29

Venlafaxine (Effexor) gel was prepared, according to a procedure similar to that of example 9. A dosage of 150–225 mg per day was self-administered by 2 patients, including a 54 year old female patient and a 55 year old male patient. Administration was by application to the skin, for a period of at least 1 hour. No skin irritation or gastrointestinal side effects were reported. Clinical evaluation of the patients over a 15–165 day period of such transdermal administration indicated a response ranging from no clinical improvement to mild clinical improvement.

EXAMPLE 30

Propranolol (Inderal) gel was prepared, according to a procedure similar to that of example 8 to produce a gel having a strength of 40 mg of propranalol per mL of gel. A dosage of 80 mg per day was self-administered by 2 patients, including a 36 year old female patient and a 47 year old male patient. Administration was by application to the skin, for a period of at least 1 hour. No skin irritation or gastrointestinal side effects were reported. Clinical evaluation of the patients over a 100 day period of such transdermal administration indicated results comparable to those achieved with oral medication.

EXAMPLE 31

Buproprion (Wellbutrin) gel was prepared, according to a procedure described in example 5. A dosage of 150–200 mg, per day was self-administered by 3 patients, including that of example 18, and also including a 38 year old male patient and a 53 year old female patient. Administration was by application to the skin, for a period of at least 1 hour. No skin irritation or gastrointestinal side effects were reported. Clinical evaluation of the patients over a 5–45 day period of such transdermal administration indicated equivocal results.

EXAMPLE 32

Valproic acid (Depakote) gel was prepared, according to a procedure similar to that of example 4. A dosage of 1000 mg per day was self-administered by a 38 year old male patient. Administration was by application to the skin, for a period of at least 1 hour. No skin irritation or gastrointestinal side effects were reported. Clinical evaluation of the patients over a 30 day period of such transdermal administration indicated results comparable to those achieved with oral medication.

EXAMPLE 33

Valproic acid (Depakote) gel was prepared according to the procedure of example 11. A dosage of 500–1000 mg was self administered by two male patients, ages 41 and 49. Administration was by application to the skin, for a period of at least one hour. Significant skin irritation occurred with one patient, but no gastrointestinal side effects were reported. Clinical evaluation of the patients over a period of two months revealed improvement, but upon longer term follow-up it appeared that other factors may have been responsible. After 28 days, blood was drawn and a serum valproic acid level of 26 μg/mL was obtained for the 49 year old patient (while taking 250 mg twice daily), with a therapeutic reference range of 50–150 μg/mL. This indicated poor to fair absorption, and the dosage was raised to 500 mg twice daily, with a further improvement in clinical response. The 41 year old patient reported a good clinical response to an initial dosage of 250 mg administered twice daily, but a serum valproic acid level of only 1 μg/mL was obtained. The dosage was increased to 500 mg twice daily, and a similar serum valproic acid level was obtained. The disparity between the clinical response and the plasma level might be explained either by laboratory error or placebo effect.

EXAMPLE 34

A gel containing reboxetine (sold under the trade name Edronax) is prepared according to a procedure similar to that described in example 5 but using reboxetine in place of buproprion. The resulting mixture will be self administered by patients by application to the skin for a period of at least 1 hour. No skin irritation or gastrointestinal side effects are expected. Clinical evaluation of patients over a 5–45 day period of such transdermal administration is expected to indicate a good response to treatment.

EXAMPLE 35

Nefazodone (Serzone) gel was prepared, according to a procedure described in example 7. A dosage of 100 mg per day was self-administered by a 61 year old (male, female) patient. Administration was by application to the skin, for a period of at least 1 hour. No skin irritation or gastrointestinal side effects were reported. Clinical evaluation of the patients over a 21 day period of such transdermal administration indicated a good response to treatment.

EXAMPLE 36

1 gram of permoline tablets are crushed in a mortar and then dissolved in propylene glycol, just sufficient to effect dissolution. 3 mL of propylene glycol or 95% ethyl alcohol is added to form a paste. 6.6 mL soya lecithin is added to the mixture in the mortar. The mixture is placed in two syringes with a Luer Loc and mixed thoroughly. Each syringe is filled to 30 mL Pluronic F127 20% gel and mixed between syringes to produce a mixture having a strength of 33 mg/mL. The mixture is put in an appropriate dispensing device.

EXAMPLE 37

A 16-year-old female with an established diagnosis of Attention Deficit Disorder had been treated successfully with oral pemoline (Cylert) for about 6 months. To potentially decrease the risk of liver damage associated with long-term use, permoline prepared according to the procedure of example 36 will be administered transdermally, by application to the skin in the post auricular region for a period of at least one hour, at two sites, twice daily. No skin irritation is expected. The clinical results are expected to be comparable to those obtained with the oral medication, although the dosage may have to be adjusted upwards to achieve adequate plasma levels, and more time may be required to achieve satisfactory plasma levels.

For psychiatric patients, some have received two or more psychopharmaceuticals, and in some cases, two or more of the above examples describe different evaluations for the same period of administration of a psychopharmaceutical agent.

Of the patients who have received prescriptions for one or more of the medications as described in the examples above, each had previously demonstrated a significant intolerance to oral administration of one or more medications, prior to instituting transdermal administration. The laboratory measures of plasma blood levels described above for transdermally administered fluoxetine and carbamazepine are believed to demonstrate good absorption transdermally using lecithin organogel matrix as the vehicle. Valproic acid and sertraline do not appear to be absorbed well or reliably. Valproic acid appears to cause skin irritation in some patients necessitating discontinuation. Both the laboratory measure of Buproprion and the patient clinical responses indicated poor or equivocal absorptions and results. Patient tolerance of transdermal administration has been good to excellent. Patients in the example above who suffered very severe GI side effects using oral preparations were more tolerant of the inconvenience of rubbing on the gel than were patients who had experienced only mild to moderate side effects. In general, more highly motivated and treatment-compliant patients also had a higher rate of sustained compliance.

Patients in the examples above were evaluated by means of a structured evaluation form depicted in FIG. 1, which was completed at a frequency of at least one time per week for each patient receiving transdermal medication according to the present invention. The patients were evaluated both for all present psychiatric symptoms as well as any side effects from currently-administered medications. In general, it is believed that patients with the most clear cut and uncomplicated diagnosis of major depression experienced the best results. In general, patients with severe personality disorders or with concealed substance abuse disorders did less well.

EXAMPLE 38

1800 mg of gabapentin in powder form is dissolved with 1 mL propylene glycol in syringes with a Luer Loc. 6.6 mL of Soya lecithin is added and mixed thoroughly between syringes. The resulting material is placed in a device for dispensing measured amounts.

EXAMPLE 39

Gabapentin mixtures of 2% and 4% will be prepared by substituting 1200 mg gabapentin or 600 mg gabapentin in place of 1800 mg gabapentin, in example 38.

EXAMPLE 40

Gabapentin, prepared according to Example 38 or 39, will be combined with either 3% or 5% Lidocaine in varying ratios.

EXAMPLE 41

4% gabapentin, prepared according to Example 38 or 39, will be combined with 7% carbamazepine and 7% amitriptyline.

EXAMPLE 42

2% gabapentin, prepared according to Example 38 or 39, will be combined with 2% carbamazepine and 1% Piroxicam, which is expected to yield better penetration into muscle tissue.

EXAMPLE 43

Gabapentin, prepared according to Example 38 or 39, in concentrations ranging from 2%–6% will be combined with clonidine in concentrations between 0.2% and 0.3%.

EXAMPLE 44

A 56-year-old woman had painful upper and lower extremity spasms as a result of spastic quadriparesis resulting from an injury. Oral gabapentin, an anticonvulsant, had been administered previously, but had caused a "drugged" feeling. one of the commonly reported side effects with this agent. It was believed that use of transdermal gabapentin might provide local relief by achieving high local tissue concentrations near the site of administration without correspondingly elevated blood plasma levels. It is known that other anticonvulsants, such as carbamazepine, are useful in reducing neurogenic pain. Gabapentin's solubility in water exceeds 10%, making systemic absorption less likely. Gabapentin prepared according to the procedure of example 38 was self-administered by application to the skin in the area of pain. The patient reported moderate relief of spasms over a period of one week, with no systemic side effects and no report of skin irritation.

EXAMPLE 45

Six grams of amitriptyline powder was placed in 40 milliliters of Pluronic F127 33% gel and placed under refrigeration to dissolve. Two milliliters of ethoxy diglycol was added to 4.8 grams of carbamazepine and mixed to form a smooth paste. 16.4 grams of soya lecithin was added to the resulting paste and mixed well. The dissolved amitriptyline composition was added to the carbamazepine composition and sufficient Pluronic F127 20% was added to make 120 milliliters and the resulting composition was mixed well to yield a composition having 5% amitriptyline and 4% carbamazepine.

EXAMPLE 46

6 grams of doxepin was added to 20 milliliters Pluronic 33% F127 and put into a refrigerator to dissolve. 24 grams of ketoprofen and 12 grams of guaifenesin was added to 10 milliliters of 95% alcohol and mixed well. 26.4 milliliters of soya lecithin was added and mixed well and the doxepin composition was mixed with the ketoprofen/guaifenesin composition. The resulting mixture was added to sufficient Pluronic 33% to yield 120 milliliters. The resulting composition was mixed well to yield a composition having about 20% ketoprofen, 5% doxepin and 10% guaifenesin.

EXAMPLE 47

6 grams of doxepin was added to 26 milliliters Pluronic 33% and refrigerated to dissolve. 2 milliliters ethoxy diglycol was added 4.8 grams carbamazepine and mixed. The resultant mixture was added to 24 grams ketoprofen and six milliliters alcohol and the result was mixed well. 26.4 milliliters soya lecithin was added to the ketoprofen composition and mixed well. The doxepin composition was mixed with the carbamazepine/ketoprofen composition and sufficient Pluronic 33% was added to yield 120 milliliters. The resultant composition was mixed well to yield a composition having about 20% ketoprofen, 4% carbamazepine and 5% doxepin.

EXAMPLE 48

0.15 grams sildenafil was crushed and strained and dissolved in 5 milliliters Pluronic 20% F127 and mixed between syringes. 2.2 milliliters of soya lecithin was added and mixed. Sufficient Pluronic 20% was added to yield 10 milliliters and the resultant composition was mixed well to yield a composition having the strength of about 15 milligrams per milliliter.

EXAMPLE 49

A mixture of Sildenafil 15 mg/ml was applied to the penis and scrotum of a 51 year old male. An immediate and strong erection resulted with sexual stimulation, without any irritation or burning. It is believed the composition will possess the therapeutic results claimed for orally administered Sildenafil, without any time delay, without any systemic GI side effects, and possibly without the degree of drug interaction with nitrates used in cardiac disease. It is believed that this will contribute both to the convenience of use of the pharmaceutical and to its safety.

EXAMPLE 50

Compositions according the examples 45 through 47, 53, 55 were transdermally applied to numerous patients, for the purpose of treating pain including as described in other examples herein, with the results summarized in Table I below. The meaning of certain entries in Table I is indicated in Table II below. Blank results indicate no treatment at the pertinent site for this patient. Where a given line of Table I shows more than one site, one "best" (biggest pain relief) result if shown in bold.

TABLE 1

| Patient | Age | Gender | Surgery | Pain | ketoprofen | gabapentin | piroxicam | doxepin | carbamazepine | amitriptyline | guaifenesin | Duration | Shoulder | Back | Neck | Elbow | Knee | Wrist | Arm | Ankle | Hip | Leg |
|---|---|---|---|---|---|---|---|---|---|---|---|---|---|---|---|---|---|---|---|---|---|---|
| | | | | | | | | | Medication Wt. % in lecithin organogel | | | | | | | Result (Best result in Bold) | | | | | | |
| A | 50 | 2 | 2 | 3 | 10 | 3 | 4 | | | | | 2 | | 0 | | 2.0 | | | | | | |
| B | 61 | 1 | 1 | 3 | | | | 5 | | | | 4 | 2.0 | 2.0 | 2.0 | 2.0 | | | | | | |
| B | 61 | 1 | 1 | 3 | | | | | 4 | | | 12 | | | | | | | | | | 1.0 |
| B | 61 | 1 | 1 | 3 | 10 | 4 | 3 | | | | | 6 | | 1.0 | | | | | 3.0 | | | |
| C | 41 | 2 | 1 | 2 | | | 1 | | 4 | | | 2 | | | .0 | | | | | | | |
| D | 53 | 1 | 2 | 1 | 10 | 4 | | 5 | | 5 | | 1 | 1.0 | 2.0 | | | 1.5 | | | | | |
| E | 57 | 2 | 2 | 3 | 10 | 4 | 1 | | | | 1 | 1 | | 2.0 | | | | 1.0 | | | | |
| E | 57 | 2 | 2 | 3 | 10 | 4 | 3 | 5 | | | | 2 | 2.0 | 2.0 | | | | | 1.5 | | | |
| F | 38 | 2 | 2 | 3 | | 4 | | 10 | 5 | | 5 | 2 | 2.0 | | | 3.0 | | | 1.0 | | | |
| F | 38 | 2 | 2 | 3 | 10 | 4 | | 5 | 4 | | | 8 | 2.0 | | | | | | | | | |
| F | 38 | 2 | 2 | 3 | 20 | 4 | | 5 | 4 | | | 4 | | | | | | | | | | |
| G | 39 | 1 | 1 | 2 | 10 | 4 | 1 | | | | | 6 | | 2.0 | | | 3.0 | | | | | |
| H | 61 | 1 | 1 | 3 | 10 | 4 | 3 | 5 | | | 10 | 4 | | | | | | | | | | |
| I | 49 | 1 | 1 | 3 | | | 3 | | 5 | | | 12 | | 1.5 | | | | 2.0 | | | | |
| I | 49 | 1 | 1 | 3 | | | | | 4 | | | 1 | | | | | | 1.0 | | | | |
| I | 49 | 1 | 1 | 3 | | | 4 | | 5 | | | 2 | | | | | | 3.0 | | | | |
| J | 54 | 1 | 1 | 3 | | | | 5 | | 5 | | 2 | 4.0 | | | | | | .0 | | | |
| K | 40 | 2 | 2 | 3 | | | 3 | 6 | | | | 2 | 1.0 | 3.0 | | | | | .0 | | | |
| K | 40 | 1 | 2 | 2 | 10 | | 3 | 5 | | | | 6 | 1.0 | | | | | | | | | |
| L | 55 | 2 | 2 | 2 | 10 | 4 | | 4 | 5 | 5 | | 4 | 1.5 | 3.0 | | | | | | 2.0 | | 2.0 |
| L | 55 | 1 | 1 | 1 | | | | | | | | 8 | 3.0 | | | | | .0 | | | | |
| M | 38 | 2 | 2 | 2 | 20 | 2 | 1 | | | | | 6 | 3.0 | 3.0 | 4.0 | | 1.0 | | | | 1.5 | |
| N | 47 | 2 | 1 | 2 | 10 | 4 | | | | | | 2 | .0 | | 2.0 | | | 2.0 | | | | |
| N | 47 | 2 | 2 | 2 | 20 | 4 | 3 | | | | | 3 | 2.0 | | 3.0 | | | | | | | |
| O | 57 | 2 | 1 | 2 | 10 | 4 | | 5 | | | | 2.0 | 1.0 | | | | | | | | | |
| O | 57 | 1 | 2 | 2 | 15 | 5 | | | | | | 24 | | .0 | | | | | | | | |
| P | 51 | 2 | 1 | 2 | 20 | | | 5 | | | | 24 | | 4.0 | | | | | | | | |
| Q | 51 | 2 | 2 | 2 | | | | 5 | | 5 | 10 | 2 | | 2.0 | | | | | | | | |
| R | 35 | 1 | 1 | 2 | | | | | 4 | | | 1 | | | | | 1.5 | | | | | |
| R | 35 | 1 | 1 | 2 | 10 | 4 | 1 | | | | | 0 | | | | | .0 | | | | | |
| S | 55 | 1 | 1 | 1 | 10 | 4 | 1 | | | | | 1 | | 1.0 | | | | | | | | |
| T | 50 | 2 | 2 | 1 | 10 | 4 | 1 | | | | | 16 | | | | | 2.0 | 1.0 | | 2.0 | | |

TABLE 1-continued

| | | | | | Medication Wt. % in lecithin organogel | | | | | | | | Result (Best result in Bold) | | | | | | | | | |
|---|---|---|---|---|---|---|---|---|---|---|---|---|---|---|---|---|---|---|---|---|---|---|
| Patient | Age | Gender | Surgery | Pain | ketoprofen | gabapentin | piroxicam | doxepin | carbamazepine | amitriptyline | guaifenesin | Duration | Shoulder | Back | Neck | Elbow | Knee | Wrist | Arm | Ankle | Hip | Leg |
| U | 45 | 1 | 2 | 2 | 10 | | 3 | | | | | 2 | | .0 | | | | | | | | |
| V | 57 | 2 | 1 | 3 | | | | | | | | 8 | | | | | 3.0 | | | | | |
| V | 57 | 2 | 1 | 3 | | | | | 6 | | | 3 | | | | | 1.0 | | | | | |
| W | 35 | 1 | 2 | 1 | 10 | 4 | 1 | | | | | 8 | | 1.0 | | | | | | | | |
| X | 46 | 1 | 1 | 3 | 10 | 4 | 1 | | | | | 8 | | 2.0 | 2.0 | 2.0 | | | | | | |
| Y | 48 | 1 | 1 | 3 | | | | 5 | 4 | | | 4 | 2.0 | 2.0 | | 1.5 | | | | | | |
| Y | 48 | 2 | 1 | 3 | 10 | 4 | 1 | 5 | | | | 4 | | | | | 1.0 | 1.5 | | | | |
| Z | 53 | 1 | 1 | 3 | 10 | 4 | 3 | | | | | 12 | | | | | | | | | .0 | |
| AA | 53 | 2 | 2 | 1 | 20 | 4 | 1 | | | | | 4 | hand | | | | | | | | | |
| BB | 58 | 2 | 1 | 3 | | | | | 4 | | 1 | 8 | | | | | | | | | 2.0 | |
| CC | 59 | 1 | 1 | 2 | 10 | 4 | 1 | 5 | | | | 2 | | 1.0 | 2.0 | | 2.0 | 2.0 | | | | |
| CC | 59 | 1 | 1 | 2 | 10 | 4 | 5 | | | | | 20 | | | 2.0 | | 3.0 | | | | | |
| CC | 59 | 1 | 1 | 2 | 10 | 4 | 3 | | | | | 1 | | | | | 3.0 | | | | | |
| DD | 58 | 1 | 1 | 2 | 10 | 4 | 3 | | | | | 12 | | | | | | 2.0 | | | | |
| EE | 45 | 2 | 2 | 3 | 10 | 4 | 3 | | | | | 24 | 1.5 | | | | 1.0 | 1.0 | | | | |
| FF | 44 | 1 | 1 | 3 | 20 | 4 | | | | | | 20 | 2.0 | | | | 1.0 | .0 | | | | |
| GG | 35 | 1 | 1 | 3 | | | | 5 | | 5 | | 4 | | | | | | 2.0 | | | | |
| GG | 35 | 1 | 1 | 3 | 20 | 5 | | 5 | 5 | | | 8 | | | | | | 2.5 | | | | |
| GG | 35 | 1 | 1 | 3 | 20 | 4 | 3 | 5 | | | | 2 | | | | 1.0 | | | | | | |
| GG | 35 | 1 | 1 | 3 | 10 | 4 | | | | | 10 | 2 | | | | 1.0 | 1.0 | | | | | |
| HH | 40 | 1 | 2 | 3 | 10 | 4 | 3 | 5 | 4 | | | 4 | | 1.0 | | | | | | 2.0 | | 1.5 |
| II | 40 | 1 | 2 | 3 | 10 | 4 | 3 | 5 | | 5 | | 8 | | 1.5 | | | | | | | | |
| II | 40 | 2 | 1 | 2 | 10 | 4 | 3 | | | | | 8 | | 2.0 | | | | | | | | |
| JJ | 45 | 1 | 2 | 2 | 10 | 4 | 1 | | | | | 2 | | 1.0 | | | | | | | | |
| KK | 37 | 2 | 2 | 2 | 10 | 4 | 3 | | | | | 8 | | 1.0 | | | 1.0 | | | | | |
| LL | 54 | 1 | 1 | 3 | | 4 | | | 4 | | | 6 | | | | | .0 | | | | | |
| LL | 54 | 1 | 1 | 3 | | 4 | | | 4 | 5 | | 2 | | | | | | | | | | |
| MM | 42 | 2 | 1 | 2 | | | | | | | | 8 | | .0 | 4.0 | | | | 2.0 | | | .0 |
| MM | 42 | 2 | 1 | 3 | 10 | | 3 | | | | | 12 | | .0 | | | | | 2.0 | | | |
| MM | 42 | 2 | 2 | 3 | | 4 | | 5 | | | | 4 | | | | | | | | 3.0 | | 1.0 |
| NN | 41 | 1 | 2 | 2 | 10 | 4 | 3 | | | | | 2 | | .0 | | | | | | | | |

TABLE II

| | | | |
|---|---|---|---|
| Gender: | 1 = male | 2 = female | |
| Surgery: | 1 = one or more surgeries | 2 = no surgeries | |
| Pain: | 1 = mild | 2 = moderate | 3 = severe-sufficient to produce observed tears |

Duration: length of treatment trial in weeks
Result:    0 = no benefit
         1 = mild benefit
         2 = moderate benefit (greater then 25% pain reduction)
         3 = major benefit (greater than 40–45% pain reduction)
         4 = almost complete relief (greater than 80% pain reduction)

Certain results drawn from the information of Table I are summarized in Table III and IV.

TABLE III

Percent reported pain relief

| Site | N (Number of data points) | None | Mild | mild-moderate | moderate | major | Total |
|---|---|---|---|---|---|---|---|
| Wrist | 13 | 16.7 | 33.3 | 8.3 | 41.7 | | |
| Shoulder | 14 | 7.1 | 21.4 | 14.3 | 42.9 | 7.1 | 7.1 |
| Elbow | 5 | | 40 | 20 | 20 | 20 | |
| Back | 25 | 24 | 32 | 8 | 28 | 8 | |
| Arm | 7 | 28.6 | 14.3 | 14.3 | 28.6 | 14.3 | |
| Neck | 11 | 9.1 | 18.2 | | 45.5 | 9.1 | 18.2 |
| Knee | 13 | 15.4 | 46.2 | 15.4 | 7.7 | 15.4 | |

TABLE IV (percent reported pain relief)

| | N | None | Mild | mild-moderate | moderate | major | Total |
|---|---|---|---|---|---|---|---|
| Best result without tricyclic | 36 | 16.7 | 36.1 | 8.3 | 27.8 | 8.3 | 2.8 |
| Best result with any tricyclic | 20 | 10 | 10 | 20 | 35 | 15 | 10 |
| Either tricyclic-sole agent | 7 | | 14.3 | 14.3 | 42.9 | 14.3 | 14.3 |
| Best result with ketoprofen gabapentin piroxicam | 25 | 16 | 44 | 4 | 28 | 8 | |
| Best result without doxepin | 43 | 18.6 | 32.6 | 14 | 23.3 | 7 | 4.7 |
| Best result with doxepin | 13 | | 7.7 | 7.7 | 53.8 | 23.1 | 7.7 |

EXAMPLE 51

A 51 year old female administered a composition prepared according to example 46, containing 20% ketoprofen, 5% doxepin, and 10% guaifenesin to her back for a period of 2 weeks. She reported moderate pain relief, lasting several hours, after each application. She reported no skin irritation nor any other side effects. Oral medications had produced no relief, and had caused significant GI side effects.

EXAMPLE 52

A 34 year old man administered a composition containing 20% ketoprofen, 4% carbamazepine, and 5% doxepin to a very severely scarred wrist that had undergone 4 surgeries for carpel tunnel syndrome. He reported moderate pain relief, lasting for several hours after each application. No other treatment, including opiate oral pain medication, had been effective in providing even minor pain relief.

EXAMPLE 53

24 grams ketoprofen and sufficient guaifenesin to result in a 10% final guaifenesin concentration, was mixed well with 10 milliliters 95% alcohol. 1200 mg gabapentin was dissolved in one ml propylene glycol in a syringe with a luer loc. 26.4 ml of soya lecithin was added to the ketoprofen-guaifenesin-alcohol mixture and mixed well. The resulting mixture was added to the gabapentin-propylene glycol mixture and mixed well. 4.8 gm of carbamazepine was combined with the resultant combination and mixed well to form a smooth paste. The resulting paste was combined with the ketoprofen-guaifenesin-alcohol-gabapentin mixture and mixed well with sufficient pluronic to yield 120 ml of a composition containing ketoprofen 20%, carbamazepine 4%, gabapentin 4%, guaifenesin 10%

EXAMPLE 54

58 year old female with damage to her cervical spinal cord with a resultant spastic quadreparesis reported moderate relief of both pain and muscle spasms when she applied a mixture prepared generally according to example 53, containing ketoprofen 20%, carbamazepine 4%, gabapentin 4%, guaifenesin 10% for a period of 8 weeks to her back and hip. She had been unable to tolerate both oral carbamazepine and oral gabapentin because of systemic side effects, including skin rash with the carbamazepine and dizziness and sedation with the gabapentin. She experienced no skin irritation nor other side effects with the transdermal formulation.

EXAMPLE 55

Six grams of doxepin powder combined with 26 milliliters pluronic and placed in the refrigerator until dissolved. 1200 mg gabapentin was mixed with 1 ml propylene glycol and placed in a syringe with luer lock. 6.6 ml of soya lecithin was added and mixed well between syringes. 24 gm of ketoprofen and 8 milliliters alcohol was mixed well between two syringes with luer loc. The doxepin mixture was mixed well with the gabapentin mixture and subsequently the ketoprofen mixture was added and mixed well. Sufficient pluronic 20% (about 54 ml) was added to yield 60 ml of a composition having about 20% ketoprofen, 4% weight percent gabapentin and 5% weight percent doxepin.

EXAMPLE 56

A 57 year old female applied a mixture, prepared generally according to example 55, containing ketoprofen 20%, gabapentin 4%, and doxepin 5% for a period of 8 weeks to her neck and reported major relief. She applied the same mixture to her shoulder and reported moderate relief. A mixture that substituted piroxicam for the doxepin produced only mild shoulder relief.

EXAMPLE 57

A 35 year old man with a history of knee injury with vascular compromise and 3 surgeries applied a mixture, prepared generally according to example 45, containing 4% carbamazepine and 5% amitriptyline to his knee, and reported mild to moderate pain relief, without skin irritation nor other side effects.

EXAMPLE 57A

A 41 year old woman with history of back surgery applied a mixture, prepared generally according to example 45, containing 4% carbamazepine and 5% gabapentin to her back for a period of 2 weeks. She reported mild pain relief.

EXAMPLE 58

A 53 year old man with a history of two total bilateral knee replacements applied a mixture, prepared generally according to example 45, containing, 4% carbamazepine and 5% amitriptyline to both knees for a period of 4 weeks. He reported no pain relief.

EXAMPLE 58A

A 54 year old man with a history of 7 back surgeries applied a mixture, prepared generally according to example 45, containing 4% carbamazepine and 5% amitriptyline to his back for a period of 2 weeks. He reported mild to moderate pain relief, over and above that he was receiving from a transdermal opiate medication (Duragesic). He reported no side effects, and specifically no skin irritation.

EXAMPLE 59

A 38 year old man with a history of shoulder strain applied a mixture, prepared generally according to example 45, containing 4% carbamazepine and 5% amitriptyline to his shoulder for a period of 2 weeks. He reported mild to moderate pain relief, and reported no skin irritation nor other side effects.

EXAMPLE 61

Sufficient carbamazepine and gabapentin was added to a combination of soya lecithin and pluronic to yield a lecithin organogel having about 4% carbamazepine and 5% gabapentin.

EXAMPLE 62

A 42 year old woman with a history of 3 back surgeries and cervical degenerative disc disease applied a mixture, prepared according to example 61, containing 4% carbamazepine and 5% gabapentin to her neck and reported total relief of pain. She reported no side effects, and no skin irritation. She noted the complete and rapid resolution of a migraine like headache at the same time. Administration of the same mixture to her arm and her wrist, affected by a diagnosed condition of reflex sympathetic dystrophy, yielded moderate pain relief.

EXAMPLE 63

3.6 grams gabapentin was dissolved with 5.4 ml ethoxy diglycol using a mortar and pestle. 9.6 grams ketoprofen and 2.7 grams piroxicam were added and the resultant composition mixed well. 19.8 milliliters soya lecithin was added and resultant mixture mixed well and added to a sufficient quantity of 20% pluronic gel to yield 90 milliliters of a composition having about 10 percent ketoprofen, 4% gabapentin and 3% piroxicam.

EXAMPLE 64

3.6 grams gabapentin was dissolved with 5.4 ml ethoxy diglycol using a mortar and pestle. 9 grams ketoprofen and 0.9 grams piroxicam were added and mixed well. 19.8 milliliters soya lecithin was added to the resultant mixture and mixed well. Sufficient amount of pluronic gel 20% was added to yield 90 milliliters of a composition having approximately 10% ketoprofen, 4% gabapentin and 1% prioxicam.

EXAMPLE 65

12 g doxepin was mixed with 50 ml Pluronic F 127 33% and placed in a refrigerator to dissolve. 12 g gabapentin was dissolved in 9 ml ethoxy diglycol and mixed to form a smooth paste. 52.8 ml of soya lecithin was added and mixed well. The doxepin/Pluronic mixture was added and mixed well. Sufficient quantity of Pluronic F 127 20% was added to produce 240 ml of a composition having about 5 wt % gabapentin and 5 wt % doxepin.

EXAMPLE 66

A 36 year old man with a knee injury involving joint surface damage and vascular comprise applied a mixture, prepared generally according to Example 65 to his knee several times per day. He reported moderate to major (40%) relief of pain that persisted for 4 to 6 hours. An earlier trial of carbamazepine-amitriptyline gel produced no relief when applied to his knee.

EXAMPLE 67

6 gm doxepin was mixed with 18 ml of Pluronic 33% to and placed in a refrigerator to dissolve. 6 gm gabapentin was ground in a mortar and pestle to a fine powder, added to 6 ml ethoxy diglycol and mixed to form a smooth paste. 12 gm guaifenesin was added and mixed well. 26.4 ml soya lecithin was added and mixed well. The doxepin/Pluronic mixture was added and mixed well. Sufficient quantity of Pluronic gel (25.2 ml of 33% Pluronic, although 30% or 20% Pluronic can be used), was added to produce 120 ml of a composition having about 5 wt % gabapentin, about 5 wt % doxepin and about 10 wt % guaifenesin.

EXAMPLE 68

A 55 year old woman with a back and shoulder injury sustained as a nursing care provider applied a mixture, prepared generally according to Example 67, to her back three times per day for a period of two weeks and achieved major relief. She applied the same mixture to her hip and leg and reported moderate to major relief. A mixture containing only doxepin provided only moderate relief to her back, and mild to moderate relief to her hip and leg. A mixture that contained only ketoprofen, gabapentin and piroxicam provided only mild relief to her back.

EXAMPLE 69

A 59 year old woman with cervical and back strain applied a mixture, prepared generally according to example 51, but without steps involving ketoprofen) containing about 5 wt % doxepin and about 10 wt % guaifenesin, to her neck for a period of two weeks, two to four times per day, and achieved total relief. She applied the same mixture to her back and achieved major to total relief.

EXAMPLE 70

4.5 gm of doxepin HCl was dissolved using 2.5 ml 95% alcohol and mixed well between syringes. It is also possible to mix the doxepin with 5 ml Pluronic 20% and place in a refrigerator to dissolve. Sufficient quantity of 20% Pluronic F127 was added to produce 90 ml of a composition having about 5 wt % doxepin. Preferably this and other disclosed compositions are protected from light.

EXAMPLE 71

A 61 year old man with injuries to his back, neck and arm applied a mixture (prepared generally according to Example 70) to his neck four times per day and achieved major relief. He applied the same mixture to his elbow and achieved moderate relief.

Based at least partially on the results described herein, a number of conclusions can be drawn. It appears doxepin is an effective neuropathic pain medication when administered transdermally and appears to be substantially free of side effects when administered by means of the gel utilized as a transport vehicle as described herein. Doxepin appears to provide about three times the positive response rate compared to at least some other pharmaceutical agents described herein, regardless of whether such other pharmaceutical agents are administered singly or in combination. Doxepin appears to be substantially more effective than amitriptyline as a neuropathic pain agent when administered transdermally. This appears to be true regardless of whether doxepin is administered as a single agent or is administered in combination with other pharmaceuticals as described herein. Carbamazepine appears to provide positive effects as a neuropathic pain agent, at least in properly selected patients. Carbamazepine appears to cause a rash in at least some patients, requiring its discontinuation. These side effects appear similar to those that are noted for oral administration of carbamazepine. Gabapentin appears to be free of side effects when administered transdermally. Although some patients appear to derive some benefit from a combination of transdermally administered ketoprofen, gabapentin, and prioxicam, the effect appears to be relatively weak compared to the effect provided by doxepin. Guaifenesini appears to provide benefit at least as an adjunctive treatment, of painful spasticity. There are some difficulties in combining guaifenesin with doxepin in gel to yield a stable non-separating mixture. In many situations it appeared that a patient who applied an analgesic gel to more than one site described different degrees of pain relief for different body parts. For the patient population described herein, amitriptyline appeared to offer only limited pain relief when administered transdermally. It appears that combining gabapentin with doxepin may offer some additional benefit. The addition of guaifenesin to doxepin may be of particular value when painful spasticity is present.

In light of the above description, a number of advantages of the present invention can be seen. The present invention provides for psychopharmaceutical and other pharmaceutical treatment using a transdermal delivery system. The invention makes it possible to provide such treatment to patients for whom oral delivery is suboptimal, such as patients who experience gastrointestinal or other side effects, patients who experience poor absorption for orally delivered pharmaceuticals and/or patients who benefit from delivery over an extended period or a relatively rapid delivery or higher rate of increase of plasma levels. The present invention is able to achieve delivery of therapeutic amounts of pharmaceuticals, for at least some patient populations, substantially without skin irritation, gastrointestinal or other side effects associated with orally-delivered pharmaceuticals, especially psychopharmaceuticals, and yields clinical benefits comparable to or greater than those received by patients to whom corresponding pharmaceuticals were administered orally. Although numerous examples of compostions which appear to be useful are disclosed herein, it is currently believed that among the most effective neuropathic pain medications are those described in examples 65, 67, 69 and 70.

A number of variations and modifications of the invention can also be used. It is believed that blood plasma levels may be increased by providing for two or more transdermal applications per day and/or applying a transdermal composition to two or more sites. At least partially on the basis of results described herein it is believed at least some other tricyclic components in a lecithin organogel will prove to be useful. In addition to amitriptyline and doxepin, examples of other tricyclic and related components include imipramine, trimipramine, clomipramine, notriptyline, protriptyline, desipramine, maprotiline, amoxapine and trazodone.

In at least one case, application of a Prozac gel formulation twice daily appeared to approximately double the plasma level. It is believed that an approach such as applying a Prozac gel formulation twice daily to two sites will yield middle range therapeutic levels of about 140–250 ng/ml. At least partially on the basis of the results described herein for fluoxetine, it is believed olanzapine (sold under the trade name Zyprexa) or a fluoxetine/olanzapine mixture in a lecithin organogel will prove useful.

Other types of psychotropic or psychopharmaceutical medications for which the described transdermal delivery may be used including psychostimulant medications. One example of a psychostimulant medication is Methylphenidate (sold under the trade name Ritalin) used in the treatment of attention deficit hyperactivity disorder (ADHD). Methylphenidate typically has a 2–4 hour duration of action necessitating frequent dosing of a patient which is particularly difficult to accomplish with children in school. It is believed that by using transdermal administration, it will be possible to achieve an extension of effective dosing throughout the day, eliminating the need for frequent oral medication administration. It is believed that transdermal administration will also eliminate peaks and valleys of blood plasma levels which, it is believed, will be more clinically effective. It is believed similar results will be obtained with other pharmaceuticals, for example, Dextroamphetamine (under the trade name Dexedrine) although it is believed the need is less acute since a time release "spansule" form of the medication is available which typically has a 5–6 hour duration of action. Another group of psychotropic medications which, it is believed, will benefit from transdermal delivery includes antipsychotic medication such as those used in the treatment in schizophrenia.

Embodiments of the invention include, but are not necessarily limited to, use by patients with enteric absorption deficits.

Although, in at least some of the embodiments described above, the pharmaceutical was provided by crushing and/or sieving tablets which include fillers or binders in addition to the pharmaceutical, the present invention can also be used by mixing, with the gel, the pharmaceutical in a relatively pure form, without filler. It is believed that this approach is likely to improve pharmaceutical delivery. In some embodiments, selected enzymes or other materials that act as transdermal delivery enhancers may be included. Carriers such as organogel lecithin matrix may be enhanced or replaced by, for example, reverse micelles (water and oil microemulsions) and/or lyposomes (lipid vesicles).

Although the present invention has been described by way of self-administered doses in the form of a gel applied to the skin by the patient, the present invention can also be implemented by providing the transdermal preparation in premeasured doses preferably in connection with an adhesive or other covering or patch so that the dosage may be administered e.g. by placing the adhesive patch on the skin of the patient. Although some embodiments of the invention have been described in connection with positioning the pharmaceutical gel on the arm of a patient, other positioning on the skin of a patient can also be used. Because, depending on the formulation, speed or duration of transdermal delivery may vary as function of skin location, in one embodiment the location of the skin to which the pharmaceutical is applied is selected so as to relatively increase or decrease the delay, speed, duration, or rate of delivery of the pharmaceutical, either with respect to a particular tissue or systemically. For example, when a rapid rise in blood serum levels is desired, a placement which enhances delivery rate, such as behind the ear, can be used. When it is desired to enhance dose or delivery rate locally, the transdermal formulation may be positioned adjacent the desired treatment area. Membranes or matrices, such as a polymer matrix, may be used to limit or control delivery rates. In addition to transdermal gel or patch delivery, delivery of the transdermal or aerosol formulation can be achieved, e.g. by administration as nosedrops, eardrops, eyedrops and/or suppositories.

Although lecithin organogel has been described as a delivery matrix, other lecithin materials can be used including lecithin combined with Pluronic Gel, or Carbopol. Although the examples above describe a gel which combines lecithin organogel with a polymer gel such as Pluronic gel, lecithin gel can be provided without combining with Pluronic gel or may be combined with other gels such as Carbopol. Although in some of the above examples, pharmaceuticals were combined with gels to provide concentration such that an effective dose occupies between about 1 mL and about 2 mL, other ratios can be used to provide for larger or smaller volume of gel per effective dose. Although a lecithin or lecithin gel carrier is described, it is believed transdermal delivery of at least some of the prescribed pharmaceuticals can be achieved using other carriers, or without using any carrier. Unless otherwise noted, an effective dose refers to a mass or volume delivered across the skin. Preferably, an effective dose is delivered to the target tissue or systemically in an amount or manner to achieve therapeutically helpful amounts or concentrations in the target tissue or systemically (such as indicated by a blood plasma level).

In one embodiment, medications dispensed in transdermal gel form will be dispensed in unit doses, such as blister packs. The gel will be extruded from the blister pack, and rubbed on the administration site. The dosage will be adjusted by varying the number of unit dose applied. This will ensure accurate dosimetry and will avoid contamination of the gel.

Although the application has been described by way of a preferred embodiment and certain variations and modifications, other variations and modification can also be used, the invention being defined by the following claims.

What is claimed is:

1. A transdermal composition comprising a psychopharmaceutical and guaifenesin in an amount effective to treat pain, and lecithin organogel.

2. The composition of claim 1, wherein said psychopharmaceutical is selected from the group consisting of sertraline, fluoxetine, carbamazepine, amitriptyline, trazodone, fluvoxamine, pemoline, pergolide, bromocriptine mesylate, propranolol, buprobrion, reboxetine, valproic acid, nefazodone and doxepin.

3. The composition of claim 1, wherein said psychopharmaceutical is doxepin.

4. A transdermal composition comprising doxepin and guaifenesin in an amount effective to treat pain, and lecithin organogel.

5. The composition of any of claims 4, further comprising Pluronic F127.

6. A transdermal composition comprising doxepin guaifenesin in an amount effective to treat pain, Pluronic F127, and lecithin organogel.

7. The composition of any one of claims 1, 4, or 6, comprising about 5 wt % doxepin.

8. The composition of any one of claims 1, 4, or 6, comprising about 10 wt % guaifenesin.

9. The composition of any one of claims 1, 4, or 6, comprising about 5 wt % doxepin and about 10 wt % guaifenesin.

10. A transdermal composition suitable for treating pain comprising about 5 wt % doxepin, about 10 wt % guaifenesin, and lecithin organogel.

11. A transdermal composition suitable for treating pain comprising about 5 wt % doxepin, about 10 wt % guaifenesin, Pluronic F127, and lecithin organogel.

* * * * *